(12) United States Patent
Dorr et al.

(10) Patent No.: US 6,270,480 B1
(45) Date of Patent: Aug. 7, 2001

(54) CATHETER APPARATUS AND METHOD

(75) Inventors: Robert T. Dorr, Tucson, AZ (US); Russell L. Spreier, Orange, CA (US)

(73) Assignee: Cancer Technologies, Inc., Tucson, AZ (US)

(*) Notice: Subject to any disclaimer, the term of this patent is extended or adjusted under 35 U.S.C. 154(b) by 0 days.

(21) Appl. No.: 09/166,666

(22) Filed: Oct. 5, 1998

(51) Int. Cl.⁷ .......................... A61M 5/178; A61M 5/00; A61M 5/32; A61M 5/31; A61M 25/00
(52) U.S. Cl. .................. 604/158; 604/115; 604/165.03; 604/177; 604/243; 604/523
(58) Field of Search .................................. 604/115, 158, 604/161, 164, 165, 170, 174, 177, 264, 272, 523, 533, 243, 159, 163

(56) References Cited

U.S. PATENT DOCUMENTS

| | | | |
|---|---|---|---|
| 1,527,291 | * | 2/1925 | Zorraquin ........................... 604/158 |
| 2,882,898 | | 4/1959 | Holmes ............................... 128/214 |
| 3,459,183 | | 8/1969 | Ring et al. ........................ 128/214.4 |
| 3,589,361 | | 6/1971 | Loper et al. ...................... 128/214.4 |
| 3,786,810 | * | 1/1974 | Pannier, Jr. et al. ................ 604/158 |
| 4,129,128 | | 12/1978 | McFarlane .......................... 128/133 |
| 4,177,809 | | 12/1979 | Moorehead ...................... 128/214.4 |
| 4,194,504 | | 3/1980 | Harms et al. .................... 128/214.4 |
| 4,198,973 | | 4/1980 | Millet ............................... 128/214.4 |
| 4,292,970 | * | 10/1981 | Hession, Jr. ........................ 604/157 |
| 4,300,553 | | 11/1981 | Seberg .............................. 128/214.4 |
| 4,353,369 | * | 10/1982 | Muetterties et al. ................. 604/272 |
| 4,362,156 | | 12/1982 | Feller, Jr. et al. ................... 604/165 |
| 4,388,074 | | 6/1983 | Seberg et al. ...................... 604/165 |
| 4,627,841 | * | 12/1986 | Dorr .................................. 604/158 |
| 4,737,143 | | 4/1988 | Russell .............................. 604/180 |
| 4,828,547 | | 5/1989 | Sahi et al. .......................... 604/110 |
| 4,834,708 | | 5/1989 | Pillari ................................ 604/165 |
| 4,898,587 | | 2/1990 | Mera ................................. 604/174 |
| 4,955,863 | | 9/1990 | Walker et al. ...................... 604/165 |
| 5,120,317 | | 6/1992 | Luther ............................... 604/158 |
| 5,120,320 | | 6/1992 | Fayngold ........................... 604/177 |
| 5,147,319 | | 9/1992 | Ishikawa et al. ................... 604/174 |
| 5,149,328 | | 9/1992 | Zaha ................................. 604/177 |
| 5,163,913 | * | 11/1992 | Rantanen-Lee et al. ............ 604/177 |

(List continued on next page.)

FOREIGN PATENT DOCUMENTS

| | | | |
|---|---|---|---|
| 0 657 184 A1 | 6/1995 | (EP) | .............................. A61M/25/06 |
| WO 95/15779 | 6/1995 | (WO) | ............................ A61M/25/00 |
| WO 98/26821 | 6/1998 | (WO) | ............................ A61M/5/178 |

OTHER PUBLICATIONS

PCT International Preliminary Examination Report dated Jan. 2, 2001 for International Application No. PCT/US99/23092.
PCT Written Opinion dated Jul. 24, 2000 for International Application No. PCT/US99/23092.
International Search Report dated Dec. 22, 1999 for International Application No. PCT/US99/23092.

*Primary Examiner*—Angela D. Sykes
*Assistant Examiner*—Patricia M. Bianco
(74) *Attorney, Agent, or Firm*—Marshall, O'Toole, Gerstein, Murray & Borun

(57) ABSTRACT

A catheter apparatus includes a hollow needle having a first end and a sharpened tip at a second end. A catheter having a blunt end is telescopically received in the needle. A catheter hub is attached to the catheter and spaced from the blunt end. The catheter hub is disposed adjacent the needle hub in an elastomeric housing. A method of inserting a catheter in a patient's vein includes a step of providing a catheter apparatus in which the elastomeric housing biases the hubs, needle, and catheter in a rest position in which the catheter protrudes from the tip of the needle. The method also includes the steps of squeezing the housing to displace the catheter hub relative to the needle hub, causing the tip of the needle to protrude beyond the blunt end of the catheter, inserting the needle and catheter in the patients's vein, and releasing the housing to allow the catheter assembly to return to the rest position.

9 Claims, 2 Drawing Sheets

U.S. PATENT DOCUMENTS

| | | | |
|---|---|---|---|
| 5,267,971 | * 12/1993 | Brimhall | 604/177 |
| 5,338,306 | 8/1994 | Srivatsa | 604/165 |
| 5,355,871 | * 10/1994 | Hurley et al. | 604/159 |
| 5,385,554 | 1/1995 | Brimhall | 604/168 |
| 5,413,562 | 5/1995 | Swauger | 604/179 |
| 5,468,228 | 11/1995 | Gebert | 604/174 |
| 5,674,201 | 10/1997 | Steinman | 604/165 |
| 5,676,656 | 10/1997 | Brimhall | 604/165 |
| 5,685,852 | * 11/1997 | Turkel et al. | 604/159 |
| 5,702,371 | 12/1997 | Bierman | 604/180 |
| 5,743,882 | 4/1998 | Luther | 604/168 |
| 5,951,520 | 9/1999 | Burzynski et al. | 604/170 |

* cited by examiner

FIG. 1
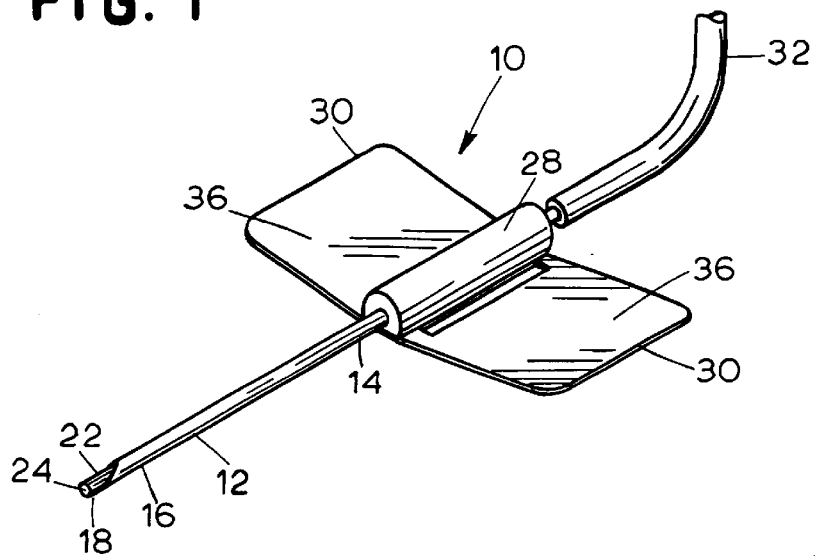
FIG. 2
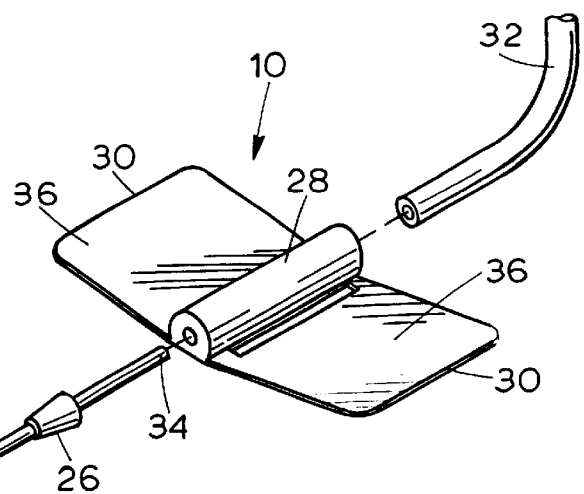
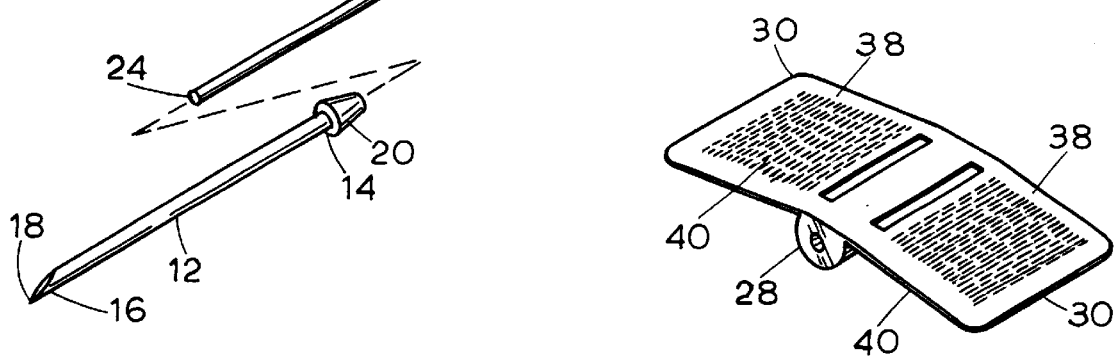
FIG. 3

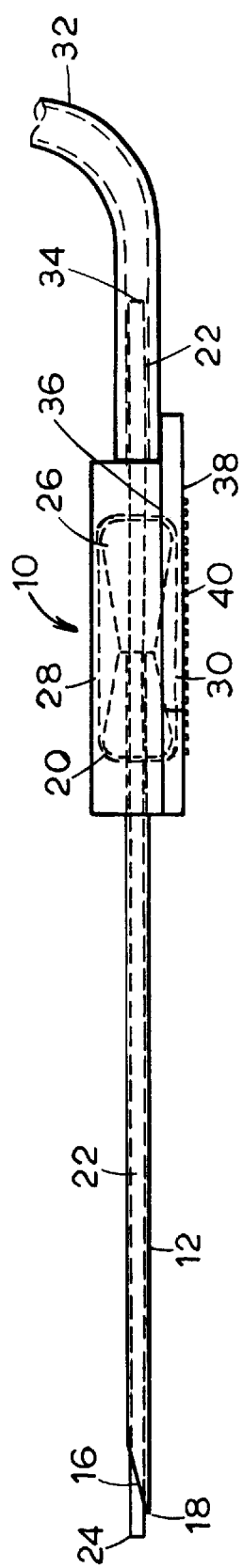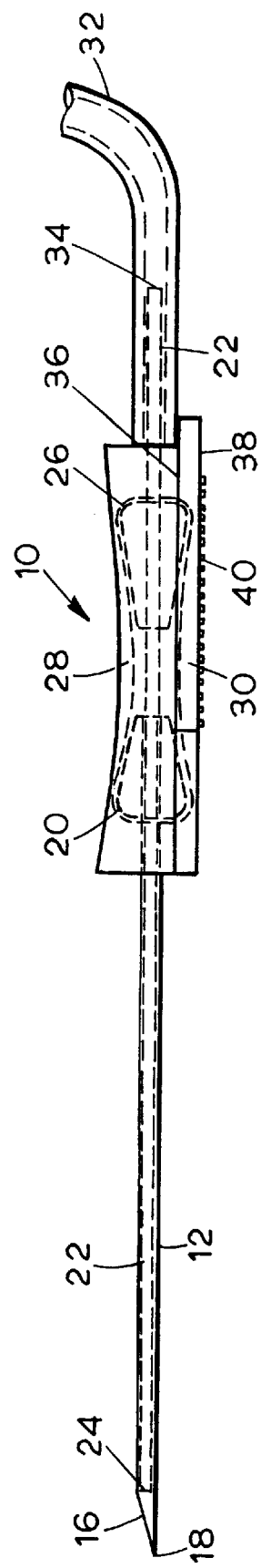
FIG. 4
FIG. 5

CATHETER APPARATUS AND METHOD

BACKGROUND OF THE INVENTION

1. Field of the Invention

This invention relates generally to medical catheters, and more particularly to catheters for providing access to blood vessels.

2. Description of Related Technology

A significant problem encountered during the administration of intravenous solutions to patients, particularly over extended periods of time, is leakage of the intravenous fluid from the vein into which it is introduced. This leakage usually results from internal laceration of the vein by an indwelling catheter or butterfly needle having a sharp tip. Subsequent leakage of solution and soft tissue damage can become a major problem, particularly if the drug being introduced into the vein is a local irritant or soft tissue vesicant.

Sharp-tipped steel scalp-vein or "butterfly" needles having flexible wings which can be taped in position on the skin of a patient are commonly used for continuous subcutaneous and intravenous medication delivery. The sharp tip of the needle can cause prolonged local irritation and pain, which may be compounded by irritation from the drug being delivered. Winged catheter assemblies may comprise a flexible cannula having a needle inserted in the cannula. The needle is used to insert the catheter into a vessel, but must be removed after the catheter is inserted. A winged infusion device comprising a catheter having a retractable sharp needle is disclosed in Dorr, U.S. Pat. No. 4,627,841, the disclosure of which is hereby incorporated by reference. The Dorr '841 patent device includes a spring for biasing a needle hub and a catheter hub towards each other and a wedge for separating the hubs. The present invention is an improvement over the Dorr '841 device in that it includes an elastomeric housing that biases a catheter hub and a needle hub towards each other. No spring or wedge are required for the present invention.

SUMMARY OF THE INVENTION

In accordance with one aspect of the present invention, a catheter apparatus includes a hollow needle having a first end and a sharpened tip at a second end. A catheter having a blunt end is telescopically received in the needle. A catheter hub is attached to the catheter and spaced from the blunt end. The catheter hub is disposed adjacent the needle hub in an elastomeric housing.

In accordance with another aspect of the present invention, a method of inserting a catheter in a patient's vein includes a step of providing a catheter apparatus including a hollow needle having a first end and a sharpened tip at a second end. A catheter having a blunt end is telescopically received in the needle and a catheter hub is attached to the catheter and spaced from the blunt end. The catheter hub is disposed adjacent the needle hub in an elastomeric housing, which biases the hubs, needle, and catheter in a rest position in which the catheter protrudes from the tip of the needle. Applying sufficient pressure to the housing displaces the catheter hub relative to the needle hub, causing the tip of the needle to protrude beyond the blunt end of the catheter and releasing the housing allows the assembly to return to the rest position. The method also includes the steps of squeezing the housing to displace the catheter hub relative to the needle hub, causing the tip of the needle to protrude beyond the blunt end of the catheter, inserting the needle and catheter in the patients's vein, and releasing the housing to allow the catheter assembly to return to the rest position.

Other objects and advantages of the invention will be apparent to those skilled in the art from a review of the following detailed description, taken in conjunction with the drawings and the appended claims.

BRIEF DESCRIPTION OF THE DRAWINGS

FIG. 1 comprises a top perspective view of a catheter apparatus according to the present invention;

FIG. 2 comprises an exploded view of the catheter apparatus of FIG. 1;

FIG. 3 comprises a bottom perspective view of the elastomeric housing and wings of the catheter apparatus of FIG. 1;

FIG. 4 comprises an elevational view of the catheter apparatus of FIG. 1, shown in a rest position; and FIG. 5 comprises an elevational view of the catheter apparatus of FIG. 1, shown in an extended position.

DETAILED DESCRIPTION OF THE INVENTION

Referring first to FIG. 1, a catheter apparatus 10 is shown in a rest position. As shown in FIGS. 1–5, the catheter apparatus 10 includes a hollow needle 12 having a first end 14. A second end 16 of the needle has a sharpened tip 18. The first end 14 of the needle is attached to a needle hub 20, disposed in an elastomeric housing 28.

A hollow catheter 22 having a first blunt end 24 and a second end 34 is telescopically received inside of the hollow needle 12. The outer diameter of catheter 22 and the inner diameter of needle 12 are selected to provide a close fit, permitting telescoping movement of the elements to be readily effected while at the same time inhibiting inward or outward fluid leakage between the catheter 22 and the needle 12. A catheter hub 26 is attached to the catheter 22 and spaced from the blunt end 24. As shown in FIGS. 4–5, the catheter hub 26 is disposed adjacent the needle hub 20 in the elastomeric housing 28. The catheter apparatus also includes a pair of flexible wings 30 which are attached to the elastomeric housing 28. The wings 30 and housing 28 may comprise a one-piece molded unit, made from a molded material such as silicone rubber. The wings 30 include a top surface 36 and a bottom surface 38. As shown in FIGS. 3–5, the bottom surface 38 includes a textured surface 40. The second end 34 of the catheter may be attached to a tube 32, such as plastic intravenous tubing. Alternatively, the end 34 of the catheter may be attached to any appropriate fitting such as a Luer-lock receptacle for supplying or receiving a fluid to or from the apparatus 10.

FIGS. 1 and 4 illustrate a rest position of the apparatus 10, in which the length of the section of catheter 22 that is within hollow needle 12 is such that blunt end 24 of the catheter protrudes slightly beyond sharp tip 18 of needle 12. Accordingly, in this condition, the sharp tip of the needle is in effect covered or retracted and incapable of penetrating any tissue that it might contact. Elastomeric housing 28 biases the catheter apparatus 10 in the rest position, with hubs 20, 26 biased towards each other and needle tip 18 kept in a retracted position, unless and until pressure is applied to elastomeric housing 28 to separate hubs 20, 26. Because of the biasing action of the elastomeric housing 28, no spring is required for biasing the apparatus 10 in the rest position.

FIG. 5 illustrates an extended position of the catheter apparatus 10, which may be obtained by applying sufficient pressure to the middle area of housing 28, such as by applying moderate pressure by squeezing the housing 28 between two fingers. Wings 30 may be folded upright prior to squeezing the housing 28, so that the textured surface 40 of the wings are squeezed, which transmits pressure to the housing 28. When housing 28 is squeezed, needle hub 20 and catheter hub 26 are separated from each other. The relative movement of the hubs 20, 26 causes the catheter 22 to move relative to needle 12, allowing the sharp tip 18 of the needle 12 to be exposed. Releasing the pressure on elastomeric housing 28 allows the catheter apparatus 10 to return to the rest position, with needle tip 18 in a retracted position. No wedge or other mechanical device is needed for squeezing the housing 22 to move the apparatus into the extended position, or to return the device to the rest position.

To use the apparatus 10 for inserting the catheter 22 into a patient's vein, the user holds the apparatus 10, folds the wings 30 upright, and applies pressure to the housing 28 by squeezing the textured surface 40 of the wings and the housing 28 between two fingers. This causes the apparatus to move into the extended position, with sharp tip 18 of the needle exposed. The sharp tip 18 may then been inserted through the patient's skin, and into a vein. Once the needle 12 and catheter 22 have been inserted in the vein, the user places the housing 28 in position on top of the patient's skin, and releases the housing 28 to allow the apparatus 10 to return to the rest position. Bottom surface 38 of the wings are then placed on the patient's skin, and the wings 30 may then be used to tape or otherwise removably secure the apparatus 10 to the body of the patient in a conventional manner.

The catheter apparatus 10 of the invention provides a number of advantages in use. Because in its rest position only the blunt end 24 of the catheter can come into contact with the vein wall or other tissue, the risk of laceration or injury to a vein or other tissue in which the needle is inserted is greatly reduced. The apparatus 10 is thus suitable for extended periods of use. Further, the fact that the apparatus 10 does not present a sharp end except when it is intentionally manipulated to do so, and the fact that a sharp needle does not need to be removed from the apparatus after insertion in a patient's vein, reduce the possibility of accidental injury or contamination to attending personnel during use or disposal of the apparatus. The design of the apparatus 10 including the elastomeric housing 28 is also an improvement over prior art catheter devices in that no springs, wedges, or other mechanical devices are required for holding the apparatus 10 in a rest position with the needle 12 retracted or for moving the apparatus into an extended position with the needle 12 extended for insertion in a vein. The apparatus 10 is therefore less expensive to manufacture, simpler to operate, and more reliable than prior art designs.

The foregoing description is given for clearness of understanding only, and no unnecessary limitations should be understood therefrom, as modifications within the scope of the invention will be apparent to those skilled in the art.

We claim:

1. A catheter apparatus comprising:
   a hollow needle having a first end and a sharpened tip at a second end;
   a needle hub attached to the needle at the first end;
   a catheter having a blunt end, the catheter telescopically received in the needle; and
   a catheter hub attached to the catheter and spaced from the blunt end, the catheter hub disposed adjacent the needle hub in an elastomeric housing.

2. The catheter apparatus of claim 1 wherein the elastomeric housing biases the hubs, needle, and catheter in a rest position in which the catheter protrudes from the tip of the needle.

3. The catheter apparatus of claim 2 wherein no spring is required for biasing the apparatus in the rest position.

4. The catheter apparatus of claim 2 wherein applying sufficient pressure to the housing displaces the catheter hub relative to the needle hub, causing the tip of the needle to protrude beyond the blunt end of the catheter, and wherein releasing the housing allows the assembly to return to the rest position.

5. The catheter apparatus of claim 4 further comprising a pair of flexible wings attached to the elastomeric housing.

6. The catheter apparatus of claim 5 wherein the housing and wings comprise a one-piece molded unit.

7. The catheter apparatus of claim 6 wherein the molded unit comprises silicone rubber.

8. A method of inserting a catheter in a patient's vein comprising the steps of:
   (a) providing a catheter apparatus comprising:
      a hollow needle having a first end and a sharpened tip at a second end;
      a needle hub attached to the needle at the first end;
      a catheter having a blunt end, the catheter telescopically received in the needle;
      a catheter hub attached to the catheter and spaced from the blunt end;
      the catheter hub disposed adjacent the needle hub in an elastomeric housing, the housing biasing the hubs, needle, and catheter in a rest position in which the catheter protrudes from the tip of the needle;
      wherein applying sufficient pressure to the housing displaces the catheter hub relative to the needle hub, causing the tip of the needle to protrude beyond the blunt end of the catheter; and
      releasing the housing allows the assembly to return to the rest position;
   (b) squeezing the housing to displace the catheter hub relative to the needle hub, and causing the tip of the needle to protrude beyond the blunt end of the catheter;
   (c) inserting the needle and catheter in the patient's vein; and
   (d) releasing the housing to allow the catheter assembly to return to the rest position.

9. The method of claim 8 further comprising the step of removably securing the housing to the patient to prevent movement of the catheter assembly.

* * * * *